United States Patent
Banez

[11] 3,963,438
[45] June 15, 1976

[54] METHOD OF STERILIZING A FIBEROPTIC PROCTOSCOPE

[76] Inventor: Armin V. Banez, 510 Gypsy Lane, Suite 1, Youngstown, Ohio 44515

[22] Filed: June 21, 1974

[21] Appl. No.: 482,024

[52] U.S. Cl.............................. 21/58; 21/2; 21/87; 21/90; 128/6; 134/22 C; 134/34; 220/336
[51] Int. Cl.²...................... A61L 1/00; A61L 3/00; B08B 3/08; B08B 9/02
[58] Field of Search............... 21/58, 73, 87, 88, 90, 21/107, 83, 99; 134/22 C, 34; 220/245, 259, 324, 331, 334, 336; 128/6

[56] References Cited
UNITED STATES PATENTS

| | | | |
|---|---|---|---|
| 2,650,179 | 8/1953 | Anderson | 134/22 C |
| 2,702,767 | 2/1955 | Domingo | 134/22 C |
| 2,982,437 | 5/1961 | Wheatley | 220/324 |
| 3,024,138 | 3/1962 | Schlott | 134/34 |
| 3,072,503 | 1/1963 | Baum | 134/22 C |
| 3,482,801 | 12/1969 | Leontas | 220/331 |
| 3,536,081 | 10/1970 | Riess | 134/22 C |
| 3,739,791 | 6/1973 | Fry et al. | 21/107 |

Primary Examiner—Morris O. Wolk
Assistant Examiner—Dale Lovercheck
Attorney, Agent, or Firm—Webster B. Harpman

[57] ABSTRACT

A sterilization method for fiberoptic scopes for proctologic use having a hand-eye piece and an elongated flexible body member having an open end, an exterior surface and an interior first fluid conveying channel comprising the steps of immersing said flexible body member in a sterilizing solution, positioning the open end of said flexible body member to direct solution to emerge towards the exterior surface of another portion of said flexible body member and circulating said sterilizing solution through said fluid conveying channel in said flexible body member for a time sufficient to sterilize said fluid conveying channel and the exterior surface of said flexible body member of said fiberoptic scope.

2 Claims, 2 Drawing Figures

METHOD OF STERILIZING A FIBEROPTIC PROCTOSCOPE

BACKGROUND OF THE INVENTION

1 Field of the Invention

This invention relates to cleaning and sterilizing devices in which sterilizing fluids at room temperature are employed.

2 Description of the Prior Art

Prior sterilizing devices have generally utilized heat as in autoclaves and have comprised containers in which instruments to be sterilized can be positioned such as seen in U.S. Pat. Nos. 2,219,417 and 2,294,087. Still other prior art devices utilizing heated fluid sterilization liquids have incorporated circulating means as seen for example in U.S. Pat. Nos. 2,327,707. Still other proposals have incorporated gas sterilizers and U.S. Pat. No. 3,478,758 discloses the use of germicidal lamps in combination with a liquid bath and a drying heated air environment.

This invention eliminates many of the problems heretofore experienced in cleaning and sterilizing fiberoptic scopes as hereinabove referred to and is equally efficient in cleaning and sterilizing gastroscopes, bronchoscopes and any other type of long flexible fiberoptic scope.

SUMMARY OF THE INVENTION

A sterilizer for fiberoptic scopes having multiple fluid conveying channels therein has a container in which the body of the fiberoptic scope is positioned and the container closed between the body and the handle and manipulating portions of the scope. A filtering and circulation system communicates with the container and includes flexible tubing establishing communication with the fluid conveying channels in the scope including those by which the scope is connected to its actuating means and supplied with water, air and/or suction and light. A suitable sterilizing fluid is added to the container and the filtering and circulation system circulates the same through the scope and it's support connective means to thoroughly clean and sterilize the exterior and interior of the scope.

DESCRIPTION OF THE PREFERRED EMBODIMENT

Figure 1:
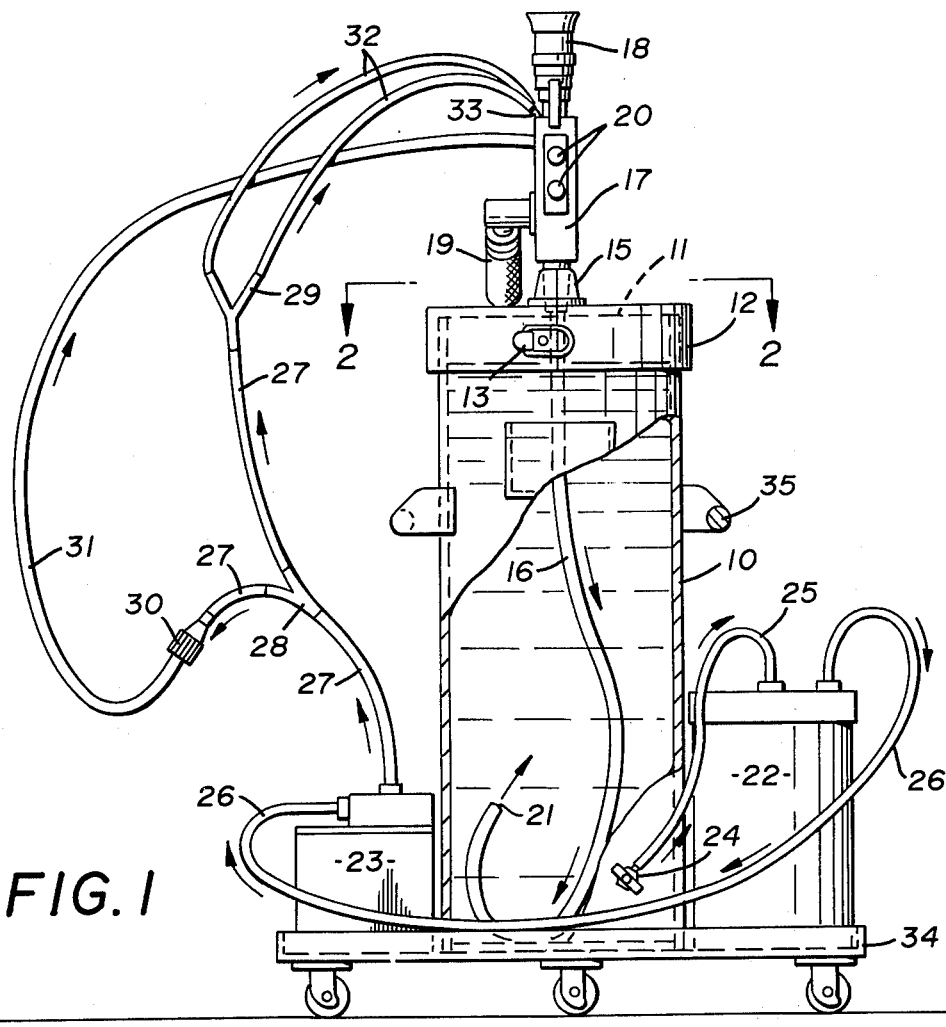
FIG. 1 is a side elevation with parts broken away and parts in cross section of a sterilizer embodying the present invention.

In the form of the invention chosen for illustration, the sterilizer, as may be seen by referring to FIG. 1 of the drawings, comprises a container 10 which is preferably cylindrical and has an open top 11 which is normally closed by a two part hinged cover 12 having a compression clamp 13 on the sides thereof opposite a hinge 14 which is disposed on a vertical axis and secured to the two parts of the cover 12.

Figure 2:
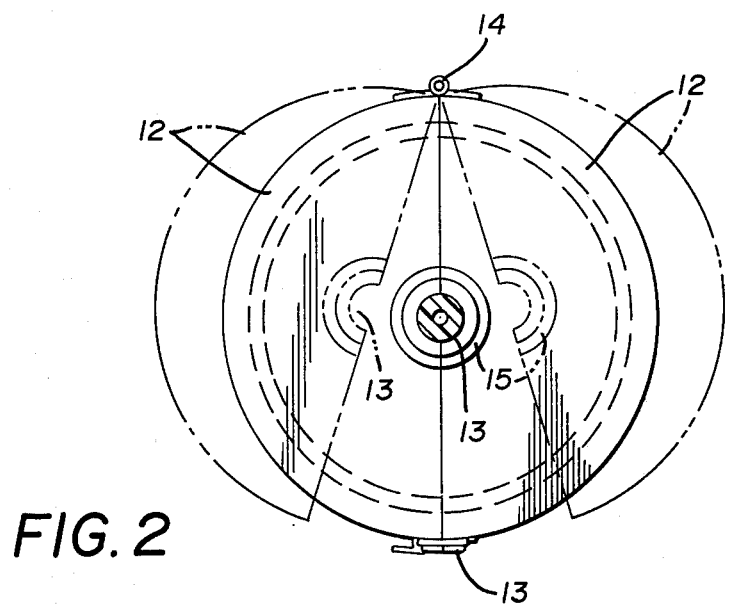
FIG. 2 is a horizontal section on line 2—2 of FIG. 1.

By referring to FIG. 2 of the drawings, a top plan view of the two part cover 12 may be seen in closed position in solid lines and in open position in broken lines and it will be observed that the two part cover 12 has a central opening 13 therein which is surrounded by an upstanding split collar 15, the two portions of which are formed integrally with the two parts of the cover 12.

By referring again to FIG. 1 of the drawings, it will be seen that when a fiberoptic scope having a long flexible body member 16 is positioned in the container 10 through the opening 13 in the two part cover 12, the manipulating and control portion 17 of the fiberoptic scope will rest on the upper end of the split collar 15. The fiberoptic scope as will be understood by those skilled in the art, includes an eye piece 18, a manipulating member 19 and several control members 20 for the control of the plurality of fluid conveying channels therein which include a water channel, a biopsy chanel and a suffusion and suction channel as well as the fiberoptic members for light transmission.

The several fluid conveying channels in the fiberoptic scope extend from the manipulating and control portion 17 thereof throughout the length of the flexible body member 16 and are open at its outermost end 21.

It will thus be seen that a sterilizing fluid such as an Aqueous Zephiran 1:750 dilution may be circulated from the container 10 through a filter 22 by a pump 23 through the several fluid conveying channels in the fiberoptic scope by way of suitable connecting tubing.

Still referring to FIG. 1 of the drawings it will be seen that there is a petcock 24 on the container 10 near the bottom thereof and that it communicates by way of a section of flexible tubing 25 with the filter 22. Filtered fluid leaves the filter 22 and communicates with the pump 23 by way of a section of flexible tubing 26 and the pump 23 which is actuated by an electric motor with means for establishing connection with a suitable power source, not shown, moves the filtered fluid through a flexible tubing 27 to a first Y connection 28 and through an extension of the tubing 27 on one side of the Y 28 to a secondary Y 29. The sterilizing fluid is divided at the first Y 28 and some of it flows into a connector 30 which is formed on the end of a flexible, elongated support member 31 which as hereinbefore referred to connects the fiberoptic scope with it's light, air, water and suction support means in normal use. As illustrated herein the tubing 27 leaving the first Y 28 establishes communication by way of the connector 20 with the fluid conveying channels in the support member 31 and flows therethrough cleaning and sterilizing the same. The flow continues as indicated by the arrows in FIG. 1 into the manipulating and control portion 17 of the fiberoptic scope and then downwardly through the control members 20 and the fluid channels in the elongated flexible body member 16 and out of the end 21 thereof thus completing a circulatory route.

Fluid leaving the other portion of the first Y 28 flows through a second portion of the tubing 27 to the second Y 29 and through two sections of flexible tubing 32 which communicate with ports 33 on the manipulating and control portion 17 of the fiberoptic scope and communicate with fluid channels therein which extend through the flexible body member 16 thereof as will be understood by those skilled in the art.

It will thus be seen that the sterilizing fluid in the container 10 cleans and sterilizes the exterior of the flexible body member 16 of the fiberoptic scope and at the same time the circulation system just described cleans and sterilizes the fluid channels within the fiberoptic scope which are used for irregation biopsy, insufflation and suction when the scope is used.

It has been determined that sterilization time of 10 to 15 minutes suitably prepares the scope for use in the hospital laboratory or doctor's office. Those skilled in the art will observe that when a scope is used in surgery for procedures requiring the highest degree of asepsis the sterilizer may be used for a longer time, for example 24 hours. The sterilization times compare favorably with the time and effort required formerly to use brush cleaning procedures or the expensive time consuming gas and aeration methods that take the scope out of commission for hours and days at a time. The sterilizer has been found particularly useful in sterilizing fiberoptic scopes used in proctology procedures such as colonscopies in trans-abdominal surgery. The effectiveness of the sterilizer and it's use has been demonstrated by bacteriology laboratory tests of cultures reported as bacteria negative.

In the form of the invention chosen for illustration and description herein, the container 10, the filter 22 and the pump 23 and it's actuating motor have been shown on a portable castered movable stand 34 and for convenience in handling the container 10 is provided with handles 35.

It will thus be seen that a sterilizer particularly suitable for immersion sterilization of any type of long, flexible fiberoptic scope having fluid conveying channels therein has been disclosed which both cleans and sterilizes the exterior and the interior of the scope.

Although but one embodiment of the present invention has been illustrated and described, it will be apparent to those skilled in the art that various changes and modifications may be made therein without departing from the spirit of the invention.

Having thus described my invention what I claim is:

1. The method of sterilizing a fiberoptic scope having a hand-eye piece and an elongated flexible body member having an open end, an exterior surface and an interior first fluid conveying channel comprising the steps of immersing said flexible body member in a sterilizing solution, positioning the open end of said flexible body member to direct solution to emerge towards the exterior surface of another portion of said flexible body member and circulating said sterilizing solution through said fluid conveying channel in said flexible body member for a time sufficient to sterilize said fluid conveying channel and the exterior surface of said flexible body member of said fiberoptic scope.

2. The method set forth in claim 1 and wherein the fiberoptic scope has a fluid supply member having a secondary fluid conveying channel therein in communication with said first fluid conveying channel in said elongated flexible body member and wherein said sterilizing solution is circulated through said first fluid conveying channel and said secondary fluid conveying channel.

* * * * *